Figure 1:
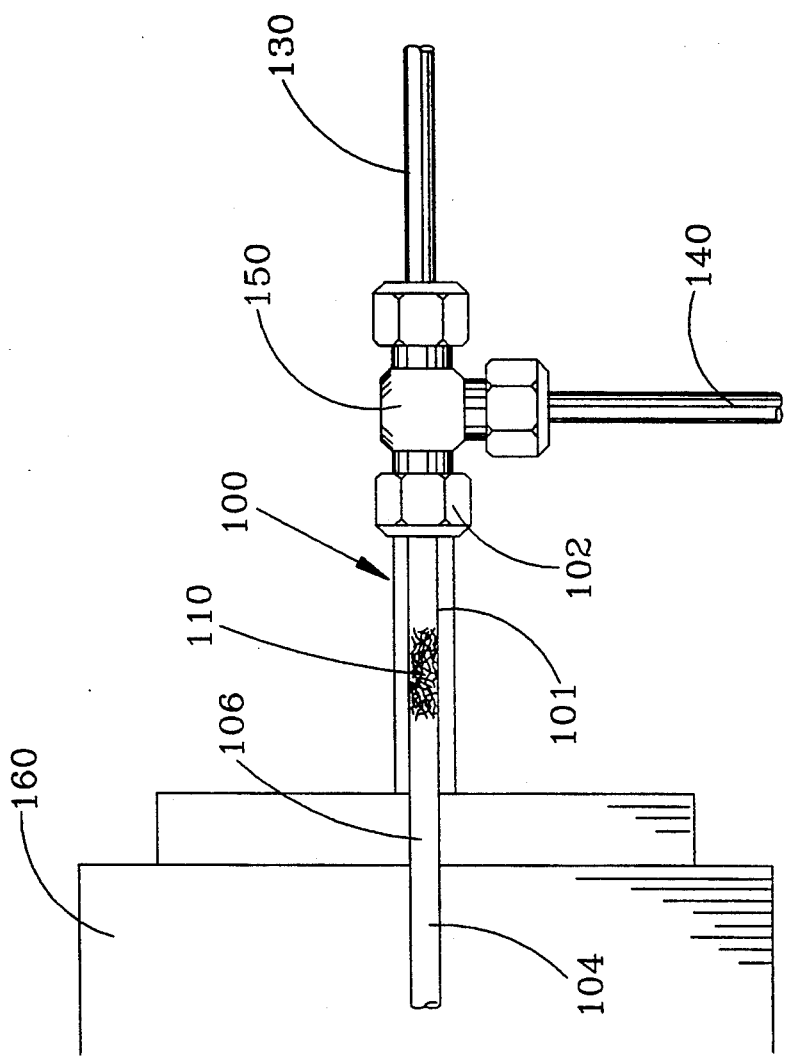

United States Patent [19]

Szinyei

[11] Patent Number: 5,315,885

[45] Date of Patent: May 31, 1994

[54] SAMPLE DISPERSING APPARATUS AND METHOD

[75] Inventor: W. Jay Szinyei, Houston, Tex.

[73] Assignee: Baker Hughes Incorporated, Houston, Tex.

[21] Appl. No.: 6,384

[22] Filed: Jan. 19, 1993

Related U.S. Application Data

[63] Continuation-in-part of Ser. No. 828,019, Jan. 30, 1992, Pat. No. 5,241,868.

[51] Int. Cl.[5] .................... G01N 30/68; G01N 31/12
[52] U.S. Cl. ................... 73/863.71; 436/154; 422/80; 73/23.2
[58] Field of Search ............ 73/23.39, 863.71, 23.42, 73/23.2; 210/692; 422/94; 436/127, 154

[56] References Cited

U.S. PATENT DOCUMENTS

| | | | |
|---|---|---|---|
| 3,612,039 | 10/1971 | Falk | 73/23.2 |
| 3,661,527 | 5/1972 | Eggertsen et al. | 436/154 |
| 3,753,654 | 8/1973 | Eggertsen | 436/154 |
| 3,859,209 | 1/1975 | Jahnsen et al. | 73/23.39 |
| 4,601,882 | 7/1986 | Benner | 422/80 |
| 4,684,251 | 8/1987 | Brouwer et al. | 356/315 |
| 4,688,436 | 8/1987 | Richon et al. | 73/863.71 |
| 4,798,805 | 1/1989 | Issenmann | 436/154 |
| 4,904,606 | 2/1990 | Forster et al. | 261/76 |
| 4,919,892 | 4/1990 | Plumb | 73/863.71 |
| 5,019,517 | 5/1991 | Coulson | 73/23.2 |
| 5,088,315 | 2/1992 | Johnson | 73/23.2 |

*Primary Examiner*—Robert Raevis
*Assistant Examiner*—George Dombroske
*Attorney, Agent, or Firm*—Sroufe, Zamecki, Payne & Lundeen

[57] ABSTRACT

An apparatus and method for dispersing a sample in a process stream is disclosed. The apparatus comprises a conduit which receives a sample at a first end and passes the sample to a pyrolysis furnace through a second end. A port is provided to admit a carrier gas. A dispersing device, preferably consisting of quartz wool, distributes the sample throughout the conduit, so that the sample may be heated by the pyrolysis furnace without coking. The method comprises the steps of receiving a sample in a conduit, dispersing the sample within a fluid carrier such that the sample is uniformly mixed throughout the fluid carrier.

7 Claims, 3 Drawing Sheets

SAMPLE DISPERSING APPARATUS AND METHOD

CROSS REFERENCE TO RELATED APPLICATION

The present application is a continuation-in-part application of the application of W. Jay Szinyei, U.S. Ser. No. 828,019, filed Jan. 30, 1992, entitled SAMPLE DISPERSING APPARATUS AND METHOD FOR USE WITH PYROLYSIS FURNACE, now U.S. Pat. No. 5,241,868.

FIELD OF THE INVENTION

The field of the invention relates generally to an apparatus and method for detecting the concentration of a fluid. Specifically, the present invention relates to an apparatus and method for dispersing a sample containing sulfur, nitrogen and other fluid compounds prior to engaging the sample with a pyrolysis furnace.

BACKGROUND OF THE INVENTION

Chemical plants, oil refineries and other industrial facilities produce fluids which present health and safety problems. In some situations, even small amounts of the fluid, for example, a few parts per million or even a few parts per billion, can constitute serious health, safety and environmental problems. Also, such fluids and gases can be a danger to workmen in the vicinity of the facility. The difficulties in detecting and determining the presence of a selected fluid in a process stream or in the environment is exceedingly difficult due to the extensive nature and the large size of industrial plants.

Thus, the detection and monitoring of fluids associated with industrial plants is highly advantageous with respect to health, safety and environmental concerns. Further, the detection and monitoring of industrial fluids can prevent other dangers such as ignition, plant failure and the like.

Further, the need to detect particular constituents in a process stream can be based on product quality, process control, regulatory requirements and financial considerations. Particular fluid constituents of interest are, for example, hydrogen sulfide and nitrogen oxides. Industrial monitoring equipment exists for all phases of industry. Particularly, a variety of equipment is available using colorimetric methods. Colorimetric monitoring is utilized in process streams and associated atmospheres in and about industrial facilities. The colorimetric equipment and methods that are prevalent include absolute darkness techniques, tape difference techniques and analog first derivative techniques. Typically using colorimetric equipment, an ambient atmosphere is passed through the apparatus whereby the fluids in question react with a color-altering material. The magnitude of the color change is proportional to the concentration of the fluid in the atmosphere.

All colorimetric methods have problems. For example, some samples not adequately dispersed cause coking on the side of the conduit when passing through a pyrolysis furnace. Also, absolute darkness techniques are subject to noise from zero fluctuation. The noise from zero fluctuations is due to the non-uniform reflectance characteristics of the colorimetric sensing media. Similarly, tape difference techniques require a zero reading. After the zero reading, a period of time must elapse between the initial reading and the final reading. The relatively long time period between readings does not take into account the nonlinearity of the sensing media and effects the response time of tape difference techniques. Analog first derivative techniques are subject to power line interferences. Further, analog first derivative techniques are limited by the current leakage in the differentiating capacitor which is typically used. Still further, the analog first derivative techniques operate in the linear portion of the response of the sensing device and require a linear response curve relationship for accurate results.

Many colorimetric analyzers generally have light sources, optics and detectors fixed in a rigid framework with light paths of the optics traversing through the ambient air. Such colorimetric analyzers require that correct alignment of the optical components be maintained during the operation of the equipment. The alignment of the optics is typically subject to environmental factors as well as mechanical problems. Examples of environmental and mechanical problems include changes in temperature, operation of equipment in high vibration environments, mechanical stress associated with typical equipment use, and the like.

Of additional concern is the environment in which the apparatus must operate. It is not unusual that the apparatus is required to be explosion proof for operation in industrial facilities. Typically, an explosion proof apparatus must be housed in a purged cabinet or housed in an explosion proof enclosure. The use of explosion proof equipment creates many problems with respect to adjustment, maintenance and calibration of the apparatus without compromising the protective environment of the explosion proof equipment.

It is, therefore, a feature of the present invention to provide a sample dispersing apparatus and method for use in combination with a pyrolysis furnace for diffusing the specimen prior to introducing the specimen into the pyrolysis furnace.

A feature of the present invention is to provide a sample dispersing apparatus and method for use in combination with a pyrolysis furnace whose scattering parameters can be changed or modified depending on the requirements of the particular analysis.

Another feature of the present invention is to provide a sample dispersing apparatus and method for use in combination with a pyrolysis furnace that provides enhanced sensitivity.

Still another feature of the present invention is utilizing a ceramic means for dispersing a sample immediately prior to entering a pyrolysis furnace.

Additional features and advantages of the invention will be set forth in part in the description which follows, and in part will become apparent from the description, or may be learned by practice of the invention. The features and advantages of the invention may be realized by means of the combinations and steps particularly pointed out in the appended claims.

SUMMARY OF THE INVENTION

To achieve the foregoing objects, features and advantages, and in accordance with the purpose of the invention as embodied and broadly described herein, an apparatus and method for dispersing a sample for use in combination with a pyrolysis furnace for measuring the concentration of a fluid in a process stream or environment is disclosed.

The apparatus for dispersing a sample for use in combination with a pyrolysis furnace for measuring the concentration of a fluid in a process stream or environment comprises a conduit having a first end for receiving the sample and a second end through which the sample passes from the conduit. The pyrolysis furnace is associated with the second end of the conduit for heating the conduit and any sample passing through the conduit. A dispersing device distributes the sample throughout the conduit such that the sample is heated in the conduit by the pyrolysis furnace without causing coking within the conduit. Preferably, the dispersing device strews the sample. The sample can be strewn by increasing the surface area of the sample, for example, on the dispersing device. An example of a dispersing device is quartz wool. Other examples of dispersing devices may be readily available or known to those skilled in the art.

The method for dispersing a sample for use in combination with a pyrolysis furnace for measuring the concentration of a fluid in a process stream or environment comprises the steps of (a) receiving a sample into a first end of a conduit having a channel there through, (b) dispersing the sample throughout the cross section of said conduit, (c) engaging the disbursed sample in the channel of the conduit with the pyrolysis furnace for initiating the pyrolization. Preferably, the dispersing step increases the surface area of the sample. Alternately, the dispersing step strews the sample essentially throughout the cross section of the channel. The strewn sample may be uniform across the diameter of the channel, e.g., linear, or may be uniform about the center or radius of the channel, e.g., Gaussian.

The method of the present invention comprises the steps of receiving a sample in a conduit, intercepting the sample for dispersing, disseminating, evaporating or strewing the sample uniformly throughout the conduit, and engaging the uniform sample with a pyrolizer. The step of intercepting the sample further comprises engaging the sample with a material porous enough or loose enough to provide the sample to flow there through in a uniform manner, and disengaging the sample from the material. More particularly, the step of engaging the sample with a material comprises the step of dispersing the sample over the surface area of the material.

Similarly, the step of intercepting the sample further comprises injecting the sample to be uniform across the reach or diameter of the conduit. Yet still more particularly, the step of interjecting the sample provides that the sample is essentially linear across the reach or diameter of the conduit.

In yet another embodiment, the step of intercepting the sample further comprises the step of interjecting the sample to be uniform about the center or radius of the conduit. More particularly, the step of interjecting the sample comprises that the sample is essentially Gaussian about the center or radius of the conduit.

Generally, the dispersing device and method of the present invention uses material that is porous or loose enough to provide that the sample flows uniformly through the material. The dispersion is initiated by the interception of the sample such that the sample is uniformly dispersed, distributed, evaporated or strewn throughout the conduit. It can be appreciated that many materials or devices may meet this criteria. For example, quartz wool is a preferred dispersant.

BRIEF DESCRIPTION OF THE DRAWINGS

The accompanying drawings which are incorporated in and constitute a part of the specification, illustrate the preferred embodiments of the invention and together with the general description of the invention given above and the detailed description of the preferred embodiment given below, serve to explain the principles of the invention.

FIG. 1 is an illustration of one embodiment of a sample dispersing apparatus and method for use in combination with a pyrolysis furnace as practiced by the present invention.

FIG. 2 is a flow diagram illustrating one embodiment of the method of the present invention.

FIG. 3 is a flow diagram illustrating additional embodiments of the method of the present invention as shown in FIG. 2.

The above general description and the following detailed description are merely illustrative of the generic invention, and additional modes, advantages and particulars of this invention will be readily suggested to those skilled in the art without departing from the spirit and scope of the invention.

DETAILED DESCRIPTION OF THE PREFERRED EMBODIMENTS

Reference will now be made in detail to the present preferred embodiments of the invention as described in the accompanying drawings.

FIG. 1 illustrates a dispensing apparatus 100. The dispensing apparatus 100 comprises a conduit 101 having an input aperture 102 and an exit aperture 104. The conduit 101 has, between the input aperture 102 and the exit aperture 104, a channel 106 there through. Engaged within the channel 106 of the conduit 101 is a diffuser 110. The conduit 101 is attached to a tee 150 at the input aperture 102, and is attached to a pyrolysis furnace 160 at the exit aperture 104. The tee 150 has a sample input port 130 and a carrier input port 140.

The sample enters the sample input port 130 passing through the tee 150. Concurrently, if appropriate, a carrier gas enters the carrier input port 140 passing through to the tee 150. The sample engages the diffuser 110 immediately prior to entering the pyrolysis furnace 160. The diffuser 110 provides that the sample is dispersed within the cross sectional area associated with the channel 106 of the conduit 101. Thus, the sample can pass through the channel 106 toward the exit aperture 102 within the pyrolysis furnace 160 without creating deposits on the channel 106 due to the heating of the sample by the pyrolysis furnace 160.

It has been found that glass or quartz wool proves to be an adequate diffuser 110 for use in the dispensing apparatus 100. The sample input port 130 can be adapted for accepting a needle from a syringe. Using the diffuser 110 within the channel 106 associated with the pyrolysis furnace 160 provides that the carrier gas picks up all the liquids and/or sulfur for mixing and for transferring them into the high temperature zone of the pyrolysis furnace 160.

One purpose of the wool diffuser 110 is to prevent liquid hydrocarbon from entering the pyrolysis furnace 160. The sample, e.g., liquid hydrocarbon, is vaporized and mixed with the carrier gas stream prior to entering the pyrolysis furnace 160, preferably by physically retaining the liquid in the hydrogen effluent stream via the wool diffuser 110.

FIG. 2 is a flow a diagram illustrating the method of the present invention. First, FIG. 2 illustrates that a sample is received in a conduit. The sample received in the conduit is intercepted. Intercepting the sample encompasses dispersing, evaporating, strewing or some other description which describes the dissemination of the sample in the conduit. Lastly, the sample which was intercepted is engaged with a pyrolysis furnace.

Figure 2:
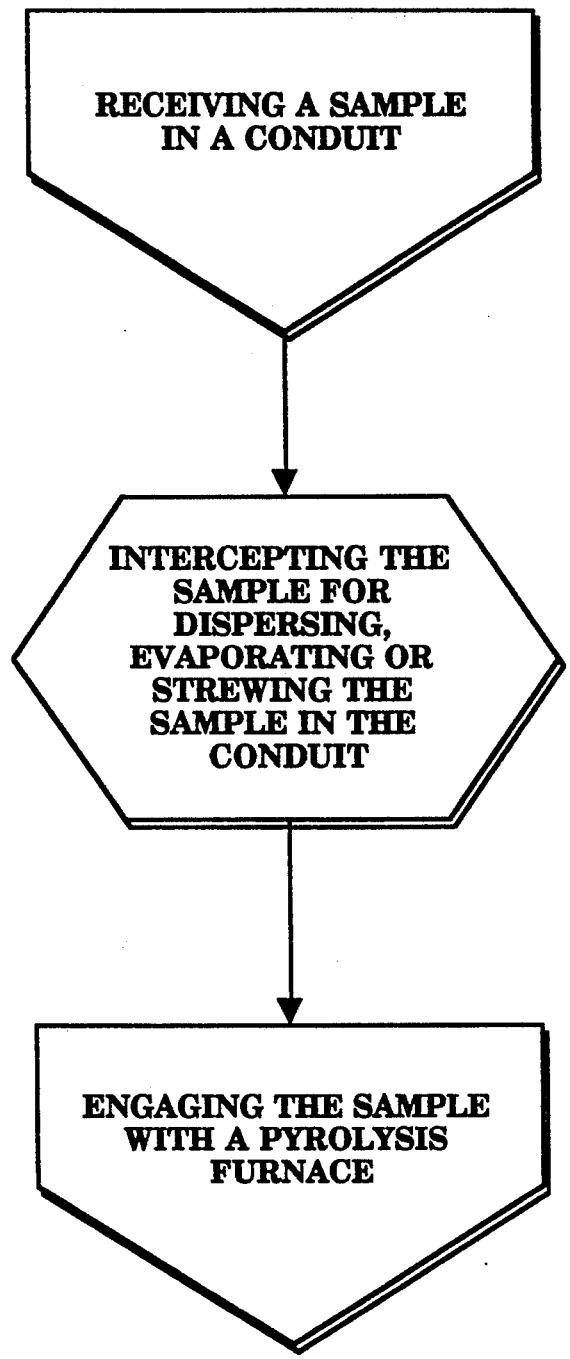
Figure 3:
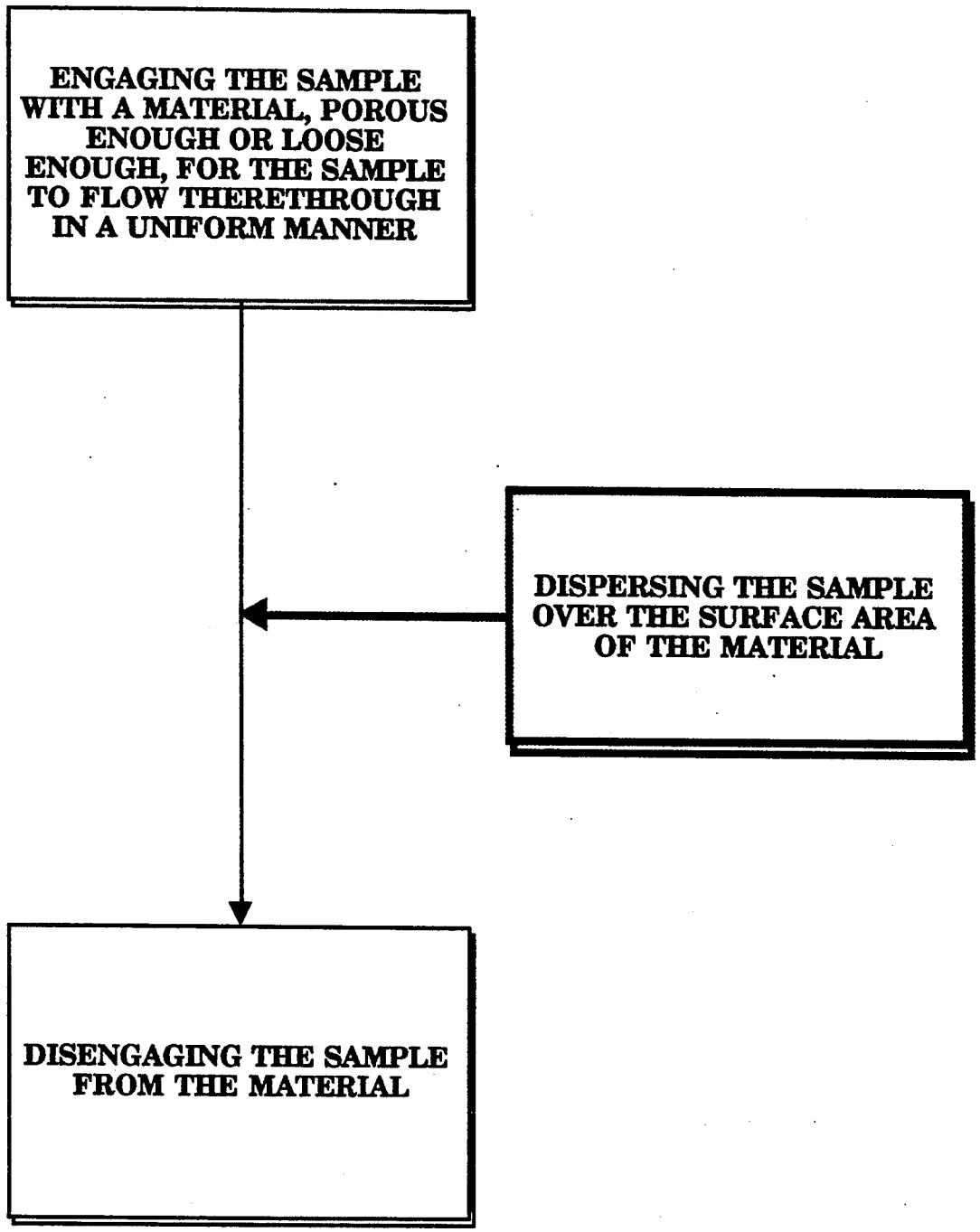

FIG. 3 illustrates additional steps which can be associated with another embodiment of the present invention as shown in FIG. 2. Particularly, FIG. 3 illustrates two different ways of intercepting the sample. First, the sample can be intercepted by engaging the sample with a porous enough or loose enough material such that the sample flows through the material in a uniform manner. After the sample flows through the material, the sample disengages from the material for dispersing, evaporating or strewing the sample in the conduit.

Yet still another embodiment of the present invention includes a three-step method of intercepting the sample. The interception of the sample may include engaging the sample with a porous enough or loose enough material for the sample to flow through the material in a uniform manner. Thereafter, the sample is dispersed over the surface area of the porous material. Lastly, the dispersed sample is disengaged with the material in the conduit.

Any dispersing material or device which meets the specific criteria of the present invention is readily adaptable for use. The material must be porous enough or loose enough to provide that the sample flow through the material is uniform. The sample is intercepted or redirected by the material. Also, the intercepted sample may be dispersed over the surface area of the material. Still further, the sample may be dispersed by the material, strewed by the material, or result in enhanced evaporation by the material. It can be appreciated by those skilled in the art that various and differing materials can be used for achieving the present invention. Also, it can be appreciated by those skilled in the art that various and sundry different devices can be used having the characteristics required for practicing the present invention.

What is claimed is:

1. An apparatus for dispersing a sample in a fluid carrier to form a sample/carrier mixture for preparing the mixture to engage a pyrolysis furnace or the like, the fluid carrier for sweeping or transporting the sample, the apparatus comprising:
   (a) a conduit having an inlet, an outlet and an intermediate section, the inlet for receiving the sample and the carrier, and the outlet for egressing the sample/carrier mixture, such that the mixture is formed in the intermediate section sufficiently remote from the pyrolysis furnace as to avoid decomposition or transformation of the sample/carrier mixture by heat from the furnace during the pendency of the sample/carrier mixture in the intermediate section, and
   (b) a dispersing device for uniformly mixing the sample within the fluid carrier regardless of the geometry of the conduit by requiring the sample and carrier to flow through a tortuous path such that said dispersing device is passive and inactive with respect to moving parts whereby the mixing results from the indirect, circuitous flow of the sample and carrier caused by said dispersing device.

2. An apparatus for dispersing a sample in a process stream or environment as defined in claim 1 wherein said dispersing device is within said conduit.

3. An apparatus for dispersing a sample in a process stream or environment as defined in claim 2 wherein said dispersing device within said conduit comprises quartz wool.

4. An apparatus for dispersing a sample in a process stream or environment as defined in claim 2 wherein said dispersing device within said conduit comprises ceramic material.

5. A method for dispersing a sample in a fluid carrier to form a sample/carrier mixture for preparing the mixture to engage a pyrolysis furnace or the like, the fluid carrier for sweeping or transporting the sample, the method comprising the steps of:
   (a) receiving a sample in the conduit,
   (b) receiving a fluid carrier in the conduit in active engagement with the sample, and
   (c) dispersing the sample within the fluid carrier by flowing the sample and fluid carrier through a tortuous path within the conduit such that the sample is dispersed, disseminated, evaporated or dissolved uniformly throughout the carrier fluid regardless of the geometry of the conduit.

6. The method as defined in claim 5 wherein the step of dispersing the sample further comprises the steps of:
   (a) engaging the sample with a material porous enough or loose enough to provide the fluid carrier to flow there through in a uniform manner, and
   (b) disengaging the sample from the material.

7. The method as defined in claim 6 wherein the step of engaging the sample further comprises the step of dispersing the sample over the surface area of the porous material.

* * * * *